US00PP09454P

United States Patent [19]

Mortensen

[11] Patent Number: Plant 9,454

[45] Date of Patent: Feb. 20, 1996

[54] GRAPE PLANT CALLED 'SOUTHERN HOME'

[75] Inventor: John A. Mortensen, Leesburg, Fla.

[73] Assignee: Florida Foundation Seed Producers, Inc., Greenwood, Fla.

[21] Appl. No.: 358,452

[22] Filed: Dec. 19, 1994

[51] Int. Cl.[6] ..... A01H 5/00

[52] U.S. Cl. ..... Plt./47.2

[58] Field of Search ..... Plt./47.1, 47.2

*Primary Examiner*—James R. Feyrer

*Attorney, Agent, or Firm*—William M. Hobby, III

[57] ABSTRACT

A new and distinct variety of grape with a unique leaf resembling the maple. This cultivar is adapted as an ornamental, dooryard grape that could be grown on arbors around patios and as borders on fences. The new grape is distinguished by vigorous growth and superior disease resistance, requiring few fungicide applications, making it environmentally compatible for use around the home. The grape is also distinguished by its foliar characteristics which make it visibly different than other commercial cultivars of grape.

3 Drawing Sheets

SUMMARY OF THE INVENTION

A new and distinct variety of grape with a unique leaf resembling the maple. This cultivar is adapted as an ornamental, dooryard grape that could be grown on arbors around patios and as borders on fences. The new grape is distinguished by vigorous growth and superior disease resistance, requiring few fungicide applications, making it environmentally compatible for use around the home. The grape is also distinguished by its foliar characteristics which make it visibly different than other commercial cultivars of grape.

BRIEF DESCRIPTION OF THE DRAWING

The accompanying color photographs show typical specimens of the plant and leaves of the new variety.

DETAILED DESCRIPTION OF THE NEW VARIETY

Figure 1:
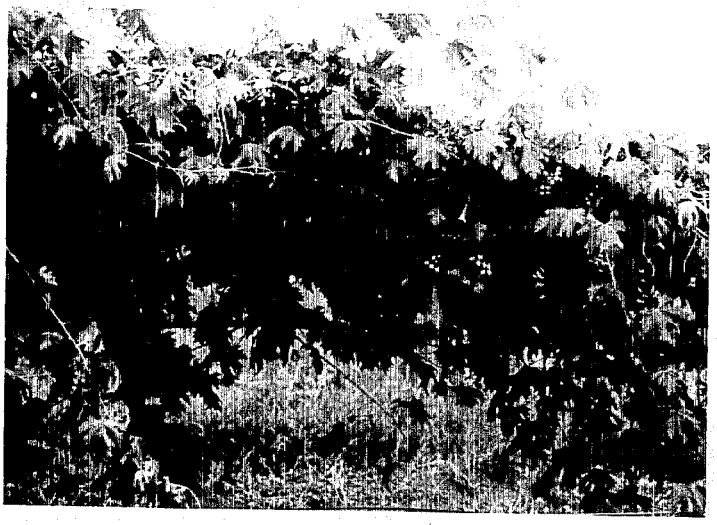
FIG. 1 is a color photograph of the present grape plant emphasizing foliage and fruit mid-season.
Figure 2:
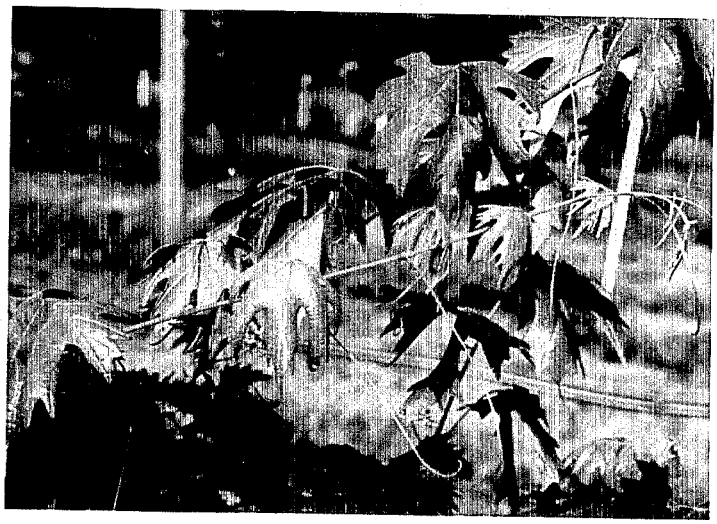
FIGS. 2 and 3 are photographs of actively growing shoot tips of the present grape emphasizing anthocyanin pigmentation in leaves and shoot tips, becoming more brilliant at node junctions and discontinuous unbranched tendrils.
Figure 3:
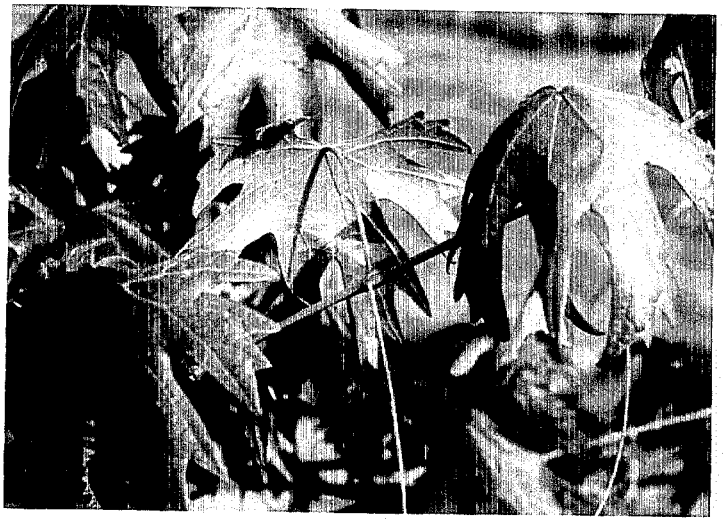
Figure 4:
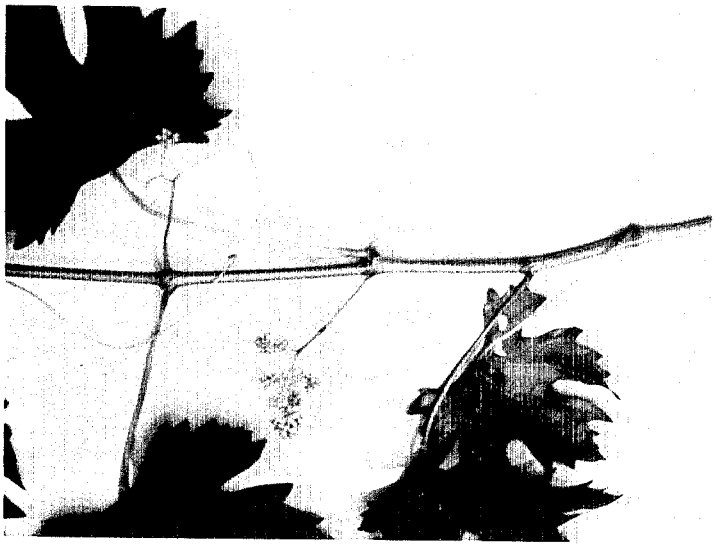
FIG. 4 is a color photograph of flower clusters in bloom detailing reproductive organs with filaments and anthers in upright position indicating self fertile flower.
Figure 5:
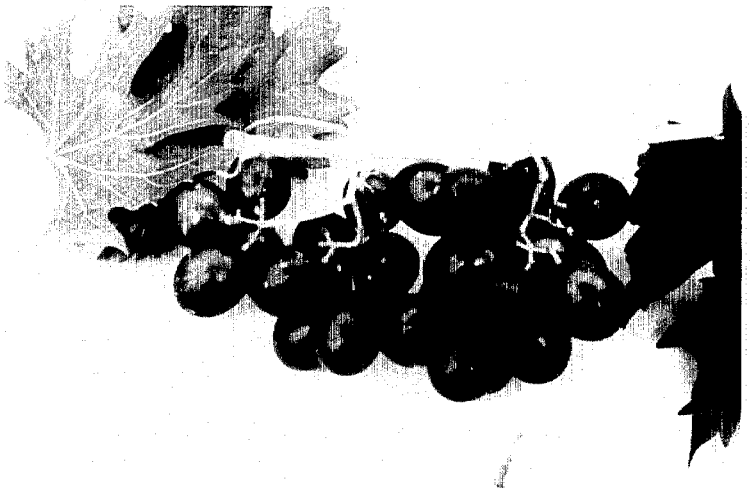
FIG. 5 is a color photograph of ripe fruit reflecting the variation in fruit shape and size and the uniform coloration at harvest.
Figure 6:
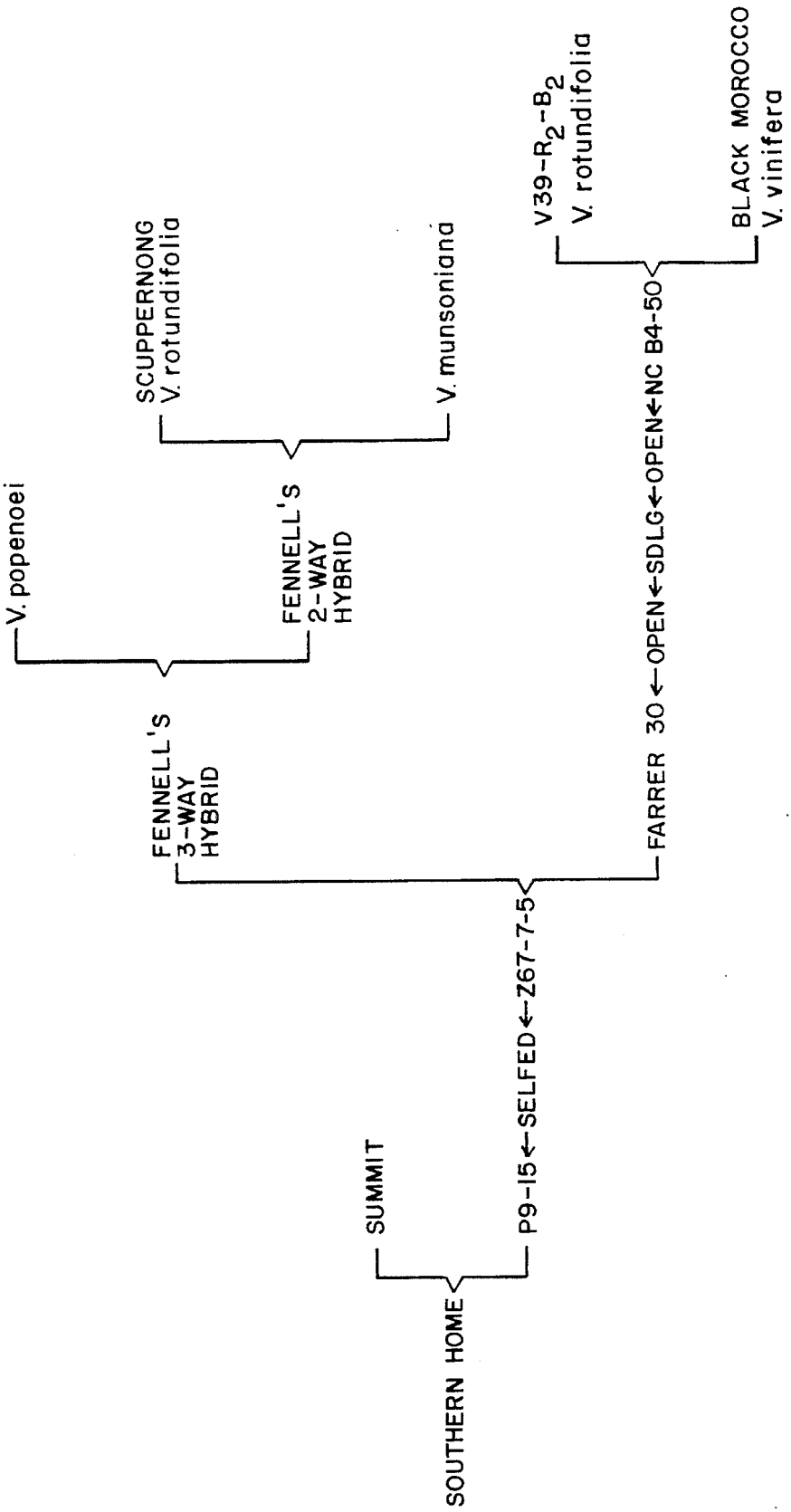
FIG. 6 is a genealogy of the present grape plant.

The present invention relates to a new and distinct cultivar of grape plant, originating from the grape breeding program at the Central Florida Research and Education Center in Leesburg, Fla. This new grape hybrid, called 'Southern Home', was one of 43 segregants from a 1979 cross between Summit muscadine and Fla. P9-15 interspecific hybrid. Upon selection for further observation and testing, the original plant was asexually propagated by cuttings made from actively growing shoots which were rooted under conventional intermittent mist in rooting beds, at the experimental facilities of the above noted institution, under my direction. The clonal stock so attained proved to be identical to the originally selected plant in all distinguishing characteristics. The genealogy as shown in FIG. 6 can be traced back to the original cross between V39-$R_2$-$B_2$ (*Vitis rotundifolia*) female and Black Morocco (*V. vinifera*) in 1916, makes Southern Home six generations removed from *V. vinifera* and is thus heavily muscadine in traits. The original seedling of Southern Home was planted in the research vineyard in 1981 and first fruited in 1984. It was first selected in 1984 because of it's striking leaf pattern, unique fruit, vigor, and disease resistance and was propagated for further trial as Fla. AA12-3.

'Southern Home' (*V. rotundifolia, munsoniana, popenoei, vinifera*) is being considered by the University of Florida as an ornamental, dooryard grape with adaptability to the Southern United States. The black fruit is of the muscadine-type and is particularly suited for the fresh fruit market and for processing into jelly. This interspecific-hybrid is unique in appearance because of its leaf shape with very deep cut sinuses, resembling, that of a maple leaf. It has potential as a dooryard grape that could be grown on arbors around patios and as borders on fences.

Type: The grape plant is a selected seedling from a cross of Summit muscadine and Fla.P9-15 interspecific hybrid. Flowers are self fertile. 'Southern Home' has excellent vigor, with semi-recumbent growth and 4 to 12 cm internodes.

Size: Grapevines can grow great distances when left unpruned and it is therefore difficult to state a specific size. It is recommended that 'Southern Home' be managed to a length of cordon not to exceed 40' on any trellis system or an overhead arbor. Height will vary from 5' to 7' when managed depending on the trellis system used. The thickness of trunk is also variable but averages about 7 cm in width.

Leaves: Leaves average 10 cm in length and 11 cm in width, resembling a maple leaf with deeply cut sinuses that are bilaterally convex in shape. Lower leaf surfaces are light green and shiny, with very slight pubescence noticeable mainly at vein junctions. Upper leaf surfaces are dark green and shiny with a slightly rugose appearance on the outer margins of leaves. Petioles are shorter than leaf blade midribs, and petiolar sinus is open. Tendrils are discontinuous along nodes, average 24 cm in length, and are unbranched. Anthocyanin pigmentation appears in petioles, lower leaf surface veins, tendrils, and newly expanded shoots and leaves becoming more brilliant at node junctions. The color, based upon The Royal Horticultural Society London colour chart for the upper leaf surface is primarily dark green (137 A) with lower leaf surface being a lighter shade of green (138 A). Leaf petioles are green (137 C) at the base, changing to red-purple (60 C) as it extends toward the leaf. Leaf midrib and veins on upper leaf surface are yellow-green (151 D). Leaf midrib and veins on lower leaf surface are primarily red-purple (60 C). Canes are primarily green (139 C) with red-purple (60 B) at node junctions.

Fruit: 'Southern Home' usually ripens at Leesburg, Fla. by Aug. 22, when it generally has reached 17–19% soluble solids and 0.29–0.39% titratable acidity. Berries ripen uniformly, with a few late blooms ripening into October or November Primary fruit may be found on the fourth and fifth nodes of the shoot, while occasional fruit may be found on the third node. Clusters are moderately loose, averaging 80.5 g and 12.2 berries per cluster. Berries are oval, averaging 18.6 mm in diameter and 23.0 mm in length with a skin thickness of 0.80 mm. The fruit average 6.7 g each. They are black with no surface bloom, but lenticels that are more prominent on 'Southern Home' berries than on Alachua result in prominent yellow-orange specks on the skin. The flesh is typically muscadine, comparable to that of Cowart or Albemarle, pale green to cream in color, translucent, medium in firmness, breaks up easily when chewed, and separates from the skin. The thick muscadine-type skin is eatable. The flavor is very aromatic, with a sweet taste. The fruit is best suited for fresh market or processing into jelly or juice. Color instability makes is undesirable for wine. With 3.4 seeds per berry weighing 5.6 g per 100 seeds, there is an average flesh to seed ratio of 33:1. This favorable ratio is comparable to that of Alachua, which is 30:1. The picking scar is moderately dry. Ripe fruit can adhere to the vine for a longer period of time than that of regular muscadine cultivars, adding to its dooryard ornamental value. Fruit storage qualities are similar to regular muscadines. The color of the fruit, based on The Royal Horticultural Society London colour chart, is black (202 A) with yellow-orange (14 D) lenticels or specks.

Flowers: The grape flowers are in clusters and the bloom has reproductive organs with filaments and anthers in upright position indicating a self fertile flower. Non-blooming flower clusters are yellow-green (145 A). In bloom, female flower parts are yellow-green (151 B). Anthers are yellow (9 B) with fresh pollen.

Pest responses: Because of 'Southern Home's' superior disease resistance few, if any, fungicide applications are required, making it environmentally compatible with the move toward reduced pesticide usage around the home. Symptoms of Pierce's disease have never been observed in Southern Home at the Central Florida Research and Education Center in Leesburg, Fla. It is highly resistant to ripe rot (*Glomerella cingulata*), bitter rot (*Melanconium fuligineum*), and black rot (*Guignardia bidwellii*). It is also completely resistant to anthracnose (*Elsinoe ampelina*) and downy mildew (*Plasmospara viticola*). Late season diseases such as angular leaf spot (*Mycosphaerella angulata*) may occur on 'Southern Home', but in such small amounts that fungicide application may not be warranted.

Asexual reproduction: Reproduction can be done by taking cuttings from actively growing shoots and placing in mist beds. Layering, by placing moist material (soil, sphagnum moss, etc.) over actively growing shoots that are still attached to the vine will also develop roots. Rooting of hardwood (dormant) cuttings, though difficult, can be obtained. In vitro micropropagation of meristem tips and nodes is another method of propagation as well as somatic embryogenesis. The original plant was asexually propagated by cuttings made from actively growing shoots which were rooted under conventional intermittent mist in rooting beds at the experimental facilities of the University of Florida, under my direction. The clonal stock so attained proved to be identical to the originally selected plant in all distinguishing characteristics.

Distinctive features: The new grape is distinguished by vigorous growth and superior disease resistance, requiring few fungicide applications to make it environmentally compatible for use around the home. The grape is also distinguished by its foliar characteristics which make it visibly different than other commercial cultivars of grape and by its vigorous growth, disease resistance and by the fruit.

The Table below shows flower type, percentage dry scar, berry size, soluble solids, type of ripening and level of disease resistance for 'Southern Home' compared with other black muscadine varieties in Leesburg and Monticello, Fla.

| Cultivar | Flower[z] | Dry scar (%) | Berry size (g) | Soluble solids (%) | Type of ripening | Disease resistance |
|---|---|---|---|---|---|---|
| | | | Leesburg Tests | | | |
| Southern Home | SF | 64.4 | 6.7 | 18.2 | Even | Excellent |
| Alachua | SF | 74.0 | 7.5 | 18.0 | Even | Very Good |
| Albemarle | SF | 82.9 | 5.8 | 19.2 | Even | Good |
| Cowart | SF | 15.0 | 7.2 | 17.6 | Uneven | Good |
| Nesbitt | SF | 31.6 | 9.8 | 17.2 | Uneven | Good |
| | | | Monticello Tests | | | |
| Southern Home | SF | 97.5 | 6.8 | 19.1 | —[y] | — |
| Alachua | SF | 98.0 | 8.0 | 17.7 | — | — |
| Loomis | F | 70.0 | 9.8 | 15.1 | — | |

[z]SF = self fertile, F = female
[y]not tested or evaluated

I claim:

1. A new and distinct cultivar of grape plant called 'Southern Home', substantially as herein illustrated and described, characterized by the unusual shape of the leaf, particularly by deep cut sinuses of the leaves resembling a maple leaf, and by the vigorous growth, disease resistance, and by the fruit.

* * * * *